United States Patent [19]

Guo

[11] Plant 4,715

[45] May 12, 1981

[54] ORCHID PLANT: GOLDEN KING

[76] Inventor: Shuh-Lih Guo, 21, Lane 626, Lin-Shen Rd., Hu-Wei Chen, Yun-Lin Hsien, Taiwan

[21] Appl. No.: 81,642

[22] Filed: Oct. 4, 1979

[51] Int. Cl.[3] ..... A01H 5/00
[52] U.S. Cl. ..... Plt./68
[58] Field of Search ..... Plt./68

*Primary Examiner*—Robert E. Bagwill

[57] ABSTRACT

A new and distinctive variety of orchid hybrid plant of the genus Phalaenopsis distinguishes itself particularly by the overall pure yellow coloration of its flowers which is rare in this genus. The new variety of orchid hybrid plant quite differs from its parents, plants of the same hybrid population, and other yellow flowered Phalaenopsis, in its unusually large size, longer blooming life, matchless yellow coloration without spots and greater profusion.

4 Drawing Figures

BACKGROUND OF THE NEW PLANT

This new orchid plant originated as a seedling of the following unpatented varieties: (Phalaenopsis Matti Shave × Phalaenopsis Orbit) × Phalaenopsis Bambo. The plant was developed by Fields Orchids, 196 N.W. 91st Street, Miami, Fla. 33150. This new orchid plant was produced by me as an outstanding member of a large population of this kind of Phalaenopsis crosses, and was named "Golden King" to identify this particular plant.

After its first discovery in 1970 with its outstanding characteristics, the original plant was placed in my greenhouse. In the subsequent years, a large number of plants have been asexually reproduced by using stem propagation method. After blooming, most of these clones reproduced are proved to be identical to the mother plant in both plant and flower with all general characteristics, and all continued to be readily distinguishable from both parent plants and the other plants in the same hybrid population.

BRIEF DESCRIPTION OF THE DRAWINGS

This new variety of orchid plant is illustrated in the accompanying drawings, in which.

DESCRIPTION OF THE NEW PLANT

Figure 1:
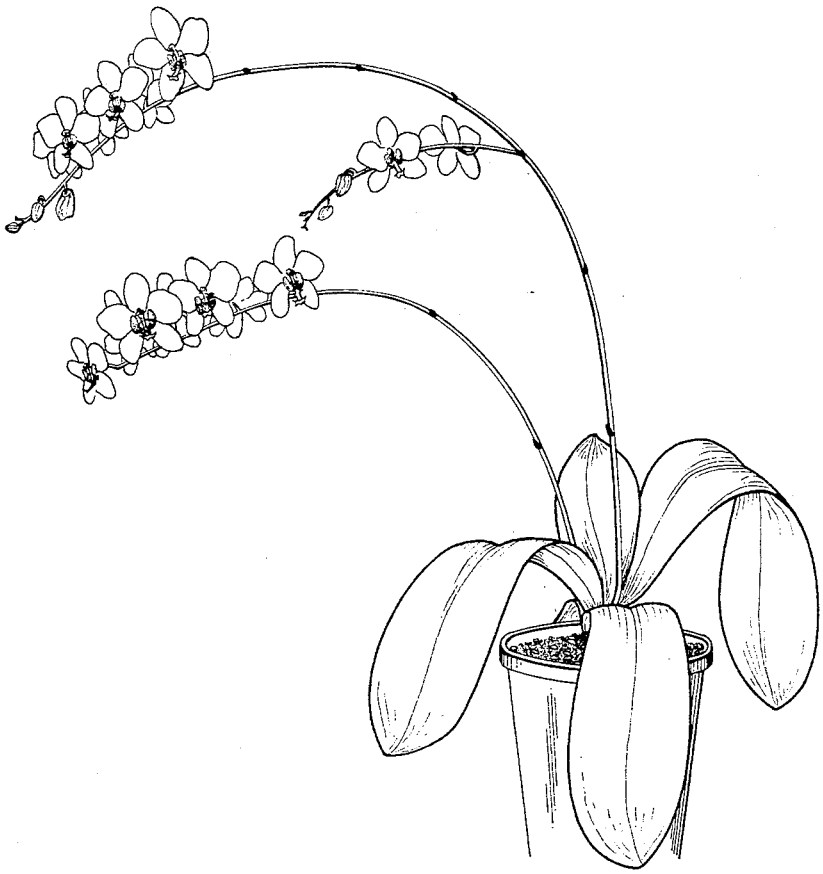
FIG. 1 is a sketch showing a typical adult plant of the cultivar.

The plant is shown in FIG. 1 accompanying this specification.

The plant: Adult plant is 15 cm to 20 cm in height.

Leaves: Leaf spread is usually 100 cm to 112 cm (from the tip of one leaf to the tip of the other).

Parentage:

*Seed parent.*—Phalaenopsis.

(*Matti Shave* × *Orbit*) *pollen parent.*—Phalaenopsis Bambo.

Classification: Botanic—Phalaenopsis stem propagation.

Form: Herbaceous.

Growth: Very vigorous.

Flower stem: 80 cm to 100 in length.

Number of leaves: The mature plant has five or more pairs of alternately opposite leaves.

Size of leaves: From 50 cm to 56 cm in length, and 14 cm to 18 cm in width on maturity. Sometimes longer and wider.

Color: The whole leaf is dark green. (R.H.S. Color Chart, No. 13 C; C C 105, Beryl Green).

DESCRIPTION OF THE FLOWER

Figure 2:
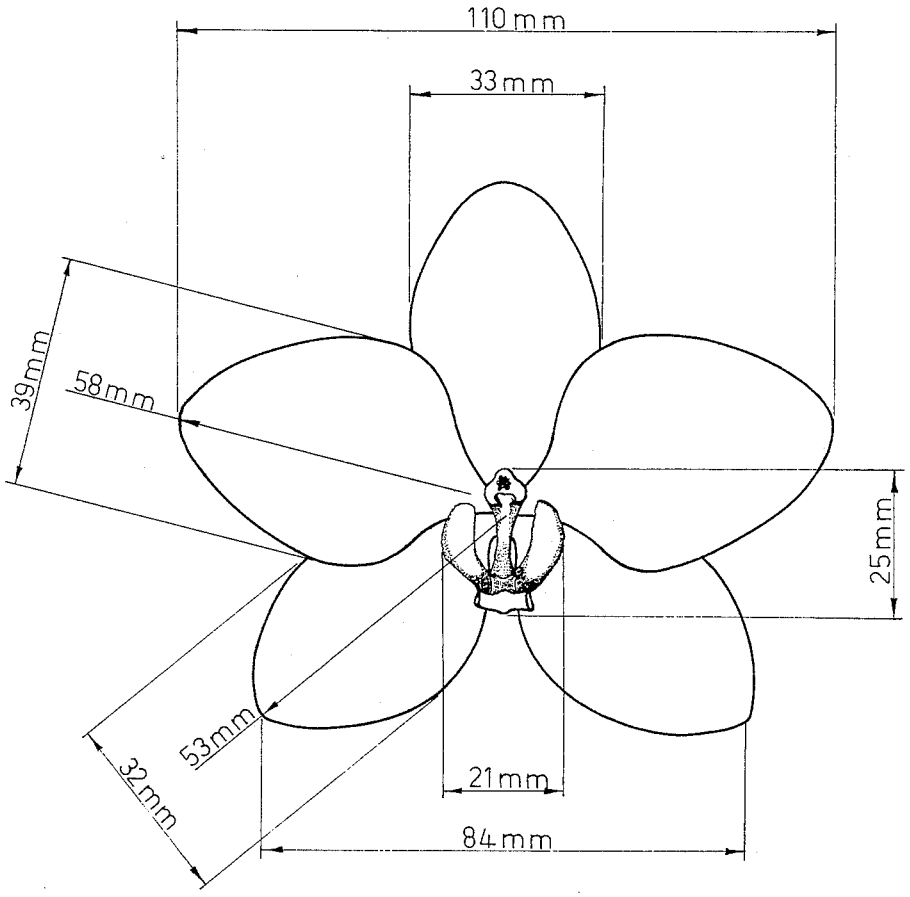
FIG. 2 is a sketch showing details of a flower of this cultivar.
Figure 3:
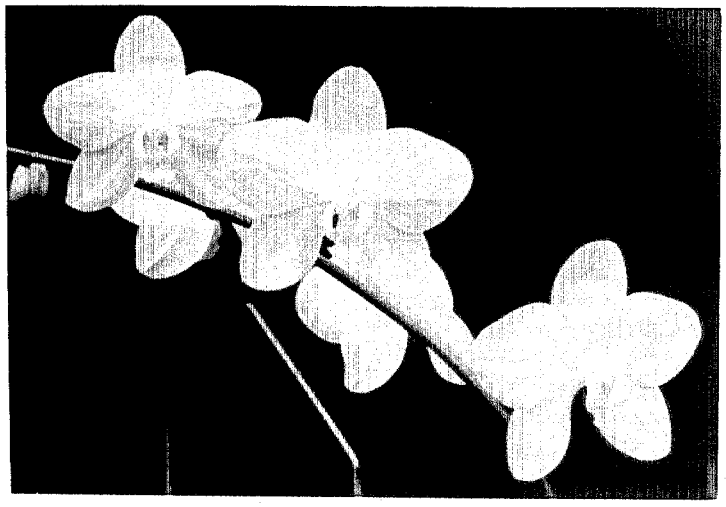
FIG. 3 is a photographic drawing showing the stem, and the full bloom of the plant in full color.
Figure 4:
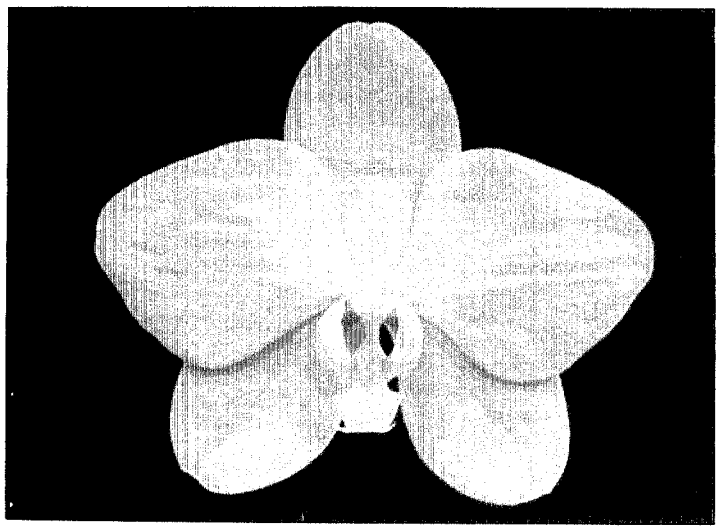
FIG. 4 is a further photographic drawing showing a flower of the plant in full color. Also shown is the matchless yellow coloration of the flower.

The unusual yellow flower is shown in FIGS. 2, 3 and 4.

Average size: Natural spread 110–120 mm.

Sepals: Spread width 84 mm. Lateral sepals 32 mm in width, 53 mm in length. Dorsal sepals 33 mm in width, 55 mm in length.

Petals: 58 mm in length, 39 mm in width.

Labellum: 25 mm in length and 21 mm in width across the center.

SHAPE OF SEPALS AND PETALS

The three sepals are in symmetrical balance to the petals and create the flower a good round shape as a whole.

Color: Both petals and sepals are uniformly pure yellow from first bloom, (R.H.S. colour chart, No. 4 B; HCC 601/1, Primrose yellow) and the yellow turns a little darker as they grow. (R.H.S. colour chart, No. 5 B; HCC 64/1, Dresden yellow) On full maturity, or with a little more sunlight, the color becomes deeper and deeper, and the surface of the flower sparkles under sunshine (R.H.S. color chart, No. 6 B; HCC 1/1, sulphur yellow).

The cultivar form "Golden King" can have twenty-four flowers on a mature well-grown plant. The flowers are well carried on one or two strong stems (see accompanying color pictures).

The substance of the flower is very heavy and waxy on its surface. The flowers can last for 8–12 weeks under optimum condition. The yellow color holds for the whole blooming period and changes to deeper yellow as a result of full maturity or exposure to more sunlight, while in most cases the colors of the Phalaenopsis species or hybrids fade out in the end of the blooming period.

As planted in Taiwan, the blooming season of this variety usually starts in early spring, mostly in February, earlier than other Phalaenopsis hybrids. Moreover, the flowers maintain firm even under occasionally cold weather in spring time.

I claim:

1. A new and distinctive variety of orchid hybrid plant of the genus Phalaenopsis substantially as herein described and illustrated, characterized particularly by its matchless and distinguished yellow flowers which are unusually large, profuse, and long-lasting when compared with other flowers of this genus.

* * * * *